(12) United States Patent
Lau et al.

(10) Patent No.: US 7,747,050 B2
(45) Date of Patent: Jun. 29, 2010

(54) SYSTEM AND METHOD FOR LINKING CURRENT AND PREVIOUS IMAGES BASED ON ANATOMY

(75) Inventors: Denny Wingchung Lau, Sunnyvale, CA (US); Yaseen Samara, Berkeley, CA (US); Thomas A. Gentles, Algonquin, IL (US); Sandy Napel, Menlo Park, CA (US); David Seungwon Paik, Palo Alto, CA (US); Vijaykalyan Yeluri, Sunnyvale, CA (US); Robert John Herfkens, Stanford, CA (US)

(73) Assignee: General Electric Company, Schenectady, NY (US)

( * ) Notice: Subject to any disclaimer, the term of this patent is extended or adjusted under 35 U.S.C. 154(b) by 569 days.

(21) Appl. No.: 11/286,548

(22) Filed: Nov. 23, 2005

(65) Prior Publication Data

US 2007/0127795 A1    Jun. 7, 2007

(51) Int. Cl.
    *G06K 9/00* (2006.01)
(52) U.S. Cl. .................. 382/128; 382/100; 382/278
(58) Field of Classification Search .......... 382/100, 382/103, 115, 128; 600/401
    See application file for complete search history.

(56) References Cited

U.S. PATENT DOCUMENTS

| | | | | |
|---|---|---|---|---|
| 5,926,568 | A * | 7/1999 | Chaney et al. | 382/217 |
| 6,488,627 | B1 * | 12/2002 | Kim | 600/437 |
| 6,909,794 | B2 * | 6/2005 | Caspi | 382/128 |
| 7,058,209 | B2 * | 6/2006 | Chen et al. | 382/117 |
| 7,136,518 | B2 * | 11/2006 | Griffin et al. | 382/133 |
| 7,158,692 | B2 * | 1/2007 | Chalana et al. | 382/294 |
| 7,194,119 | B2 * | 3/2007 | Zahlmann et al. | 382/128 |
| 7,251,345 | B1 * | 7/2007 | Han | 382/103 |
| 7,263,243 | B2 * | 8/2007 | Chen et al. | 382/294 |
| 7,346,199 | B2 * | 3/2008 | Pfaff | 382/128 |
| 2003/0153818 | A1 * | 8/2003 | Bocionek et al. | 600/300 |
| 2003/0228042 | A1 * | 12/2003 | Sinha | 382/131 |
| 2004/0120557 | A1 * | 6/2004 | Sabol et al. | 382/128 |
| 2005/0147284 | A1 * | 7/2005 | Vining et al. | 382/128 |
| 2006/0030768 | A1 * | 2/2006 | Ramamurthy et al. | 600/407 |

OTHER PUBLICATIONS van den Eisen, Petra A. et al., "Medical Image Matching—A Review with Classification" Engineering in Medicine and Biology Magazine, IEEE, Mar. 1993 vol. 12 Issue 1, pp. 26-39.*
PACS—Acute Care Settings 2003 Report; Unknown Author; KLAS Enterprises, LLC; Nov. 2003; Copyright 2002; 9 pages, pp. 162-164.

* cited by examiner

*Primary Examiner*—Matthew C Bella
*Assistant Examiner*—Eric Rush
(74) *Attorney, Agent, or Firm*—Hanley, Flight & Zimmerman, LLC

(57) ABSTRACT

Certain embodiments of the present invention provide systems and methods for correlating an acquired image with an historical image. Certain embodiments include registering an acquired image and at least one historical image according to a coordinate system, applying a metric to the acquired image and each of the historical image(s), and identifying a correlation between the acquired image and one of the historical image(s) based on the metric. Certain embodiments further include storing the correlation between the acquired image and an historical image for automatic linking of the acquired image and the historical image upon display. In certain embodiments, the acquired image and the historical image may be displayed based on the correlation. In certain embodiments, the acquired image and the historical image may be automatically linked based on the correlation. In certain embodiments, the metric analyzes the acquired image and at least one historical image based on anatomy.

15 Claims, 3 Drawing Sheets

SYSTEM AND METHOD FOR LINKING CURRENT AND PREVIOUS IMAGES BASED ON ANATOMY

BACKGROUND OF THE INVENTION

The present invention generally relates to anatomy labeling on a picture archiving and communication system (PACS). In particular, the present invention relates to anatomy labeling on a PACS to enable anatomy specific image presentation and analysis.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

A PACS may connect to medical diagnostic imaging devices and employ an acquisition gateway (between the acquisition device and the PACS), storage and archiving units, display workstations, databases, and sophisticated data processors. These components are integrated together by a communication network and data management system. A PACS has, in general, the overall goals of streamlining healthcare operations, facilitating distributed remote examination and diagnosis, and improving patient care.

A typical application of a PACS system is to provide one or more medical images for examination by a medical professional. For example, a PACS system may provide a series of x-ray images to a display workstation where the images are displayed for a radiologist to perform a diagnostic examination. Based on the presentation of these images, the radiologist may provide a diagnosis. For example, the radiologist may diagnose a tumor or lesion in x-ray images of a patient's lungs.

Computed tomography ("CT") exams may include images that are acquired from scanning large sections of a patients' body. For example, a chest/abdomen/pelvis CT exam includes one or more images of several different anatomy. Each anatomy may be better viewed under different window level settings, however. Thus, when a radiologist or other personnel is interpreting a chest/abdomen/pelvis CT exam, he or she switches among different settings to view images for different anatomy, for example.

Currently, image review workstations may not correlate image content to anatomy to facilitate presentation of relevant anatomical data. However, healthcare personnel, such as radiologists, may be interested to view information about specific anatomical structures and/or other patient data when viewing and/or interpreting patient image(s). For example, when a radiologist is viewing a CT axial image that contains the liver, he or she may want to learn about the disease processes associated with the liver or the patient's lab tests associated with the liver. Thus, an image review workstation having the capability to recognize an anatomy of interest, such as a liver, and search for and present anatomy-related information to a user would be highly desirable.

During an exam interpretation process, radiologists and/or other healthcare personnel may like to note image findings as a mechanism to compose reports. In the case of structured reports, radiologists have found that the mechanism to input data is too cumbersome. That is, since there are so many possible findings related to an exam procedure, the findings need to be categorized in some hierarchy structure. The numerous hierarchical levels and choices of selection require extensive manual manipulation from the radiologist.

For example, a chest/abdomen/pelvis CT exam may include images of the liver, pancreas, stomach, etc. If a radiologist wants to input a finding related to the liver, he or she must currently traverse through a hierarchy of choices presented in a graphical user interface before being able to identify the desired finding.

When radiologists are viewing patients' images in the exam interpretation process, sometimes they would like to view the images specific to certain organs. For example, a patient with a history of colon cancer has a CT exam that contains images of the stomach, small intestine, liver, pancreas, colon, etc. A radiologist may want to first view the images of the colon. If the colon does not demonstrate any remarkable abnormalities, then the radiologist may suspect that the reported symptoms are related to ailments in the liver and wants to view the images containing the liver. However, there is currently no method on image review workstations that enables a radiologist to view images specific to organs. A radiologist may only view images in sequential order.

Physicians, radiologists and/or other healthcare practitioners often request multiple scans for a patient over a period of time either because 1) they suspect that the patient is suffering from a particular ailment or 2) the patient is already undergoing treatment and they want to monitor his or her progress. When a radiologist is reading a patient's exam, for example, it is important for him or her to have access to the patient's previous exams, which enable the radiologist to better understand the patient and to monitor the changes that have occurred since the patient's last exam. For example, when a chest radiologist finds a nodule in the current exam, he will also look for the nodule in the previous exams, to see if there is any change in the size or volume of the nodule.

Hanging protocols automatically allow a radiologist or other user to see current and historical exams for a patient simultaneously. Currently, if a radiologist or other user identifies a nodule in an image in a current exam, the user must manually cine through previous exams to find the corresponding image at the same location, and observe the difference in images. When a patient has several previous exams, a radiologist or other user must spend a considerable amount of time to manual locate a slice in each exam. Even if image slices are to be synchronized or linked, a radiologist must first manually find the same image in each exam before enabling the synchronization for future retrieval based on DICOM information.

Thus, a method and system that improve review efficiency would be highly desirable. A method and system for better retrieval of relevant patient information and images would be highly desirable.

BRIEF SUMMARY OF THE INVENTION

Certain embodiments of the present invention provide systems and methods for image registration and correlation between a current image and a previous image based on anatomy. Certain embodiments provide an image registration system for correlating a current image with a previous image. The system includes an image processing subsystem configured to compare at least one current image and at least one previous image using a metric, wherein the image processing subsystem identifies a corresponding previous image for a current image based on the metric. The system also includes a matching table identifying the current image and the corresponding previous image, wherein the matching table is used to automatically retrieve the corresponding previous image when the current image is displayed.

In certain embodiments, the metric generates a metric value representing a degree of similarity between a current image and a previous image, and the image processing subsystem identifies a corresponding previous image for a current image based on the metric value. In certain embodiments, the image processing subsystem registers at least one current image and at least one previous image according to a coordinate system. In certain embodiments, the image processing subsystem automatically identifies a corresponding previous image for a current image upon receipt of the current image.

Certain embodiments of the system may also include a display subsystem capable of displaying the current image in conjunction with the corresponding previous image. In certain embodiments, the display subsystem is capable of displaying clinical data in conjunction with the current image and the corresponding previous image. Certain embodiments may further include an image/data storage subsystem configured to store at least one current image, at least one previous image, and/or clinical data, for example.

Certain embodiments provide a method for correlating anatomy in an acquired image with an historical image. The method includes registering an acquired image and at least one historical image according to a coordinate system, applying a metric to the acquired image and each of the historical image(s), and identifying a correlation between the acquired image and one of the historical image(s) based on the metric.

Certain embodiments further include storing the correlation between the acquired image and an historical image for automatic linking of the acquired image and the historical image upon display. In certain embodiments, the acquired image and the historical image may be displayed based on the correlation. In certain embodiments, the acquired image and the historical image may be automatically linked based on the correlation. In certain embodiments, the metric analyzes the acquired image and at least one historical image based on anatomy.

Certain embodiments provide a computer-readable storage medium including a set of instructions for execution on a processor. The set of instructions may include an image registration routine configured to register an acquired image with respect to at least one historical image, and an image mapping routine configured to map the acquired image with one of the at least one historical image based on anatomy. The image mapping routine identifies one of the historical image(s) similar to the acquired image based on a metric.

In certain embodiments, the set of instructions may further include a display routine for displaying the acquired image and the mapped historical image. In certain embodiments, the display routine automatically displays the acquired image and the historical image based on a mapping of the acquired image with the historical image. Certain embodiments may also include a mapping data structure storing a mapping between the acquired image and one of the historical image(s).

In certain embodiments, the image mapping routine automatically links the acquired image and one of the historical image(s) for display. In certain embodiments, the image mapping routine automatically identifies a mapping between the acquired image and one of the historical image(s) upon receipt of the acquired image. In certain embodiments, the image mapping routine further identifies clinical information relevant the acquired image and/or the historical image(s), for example.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
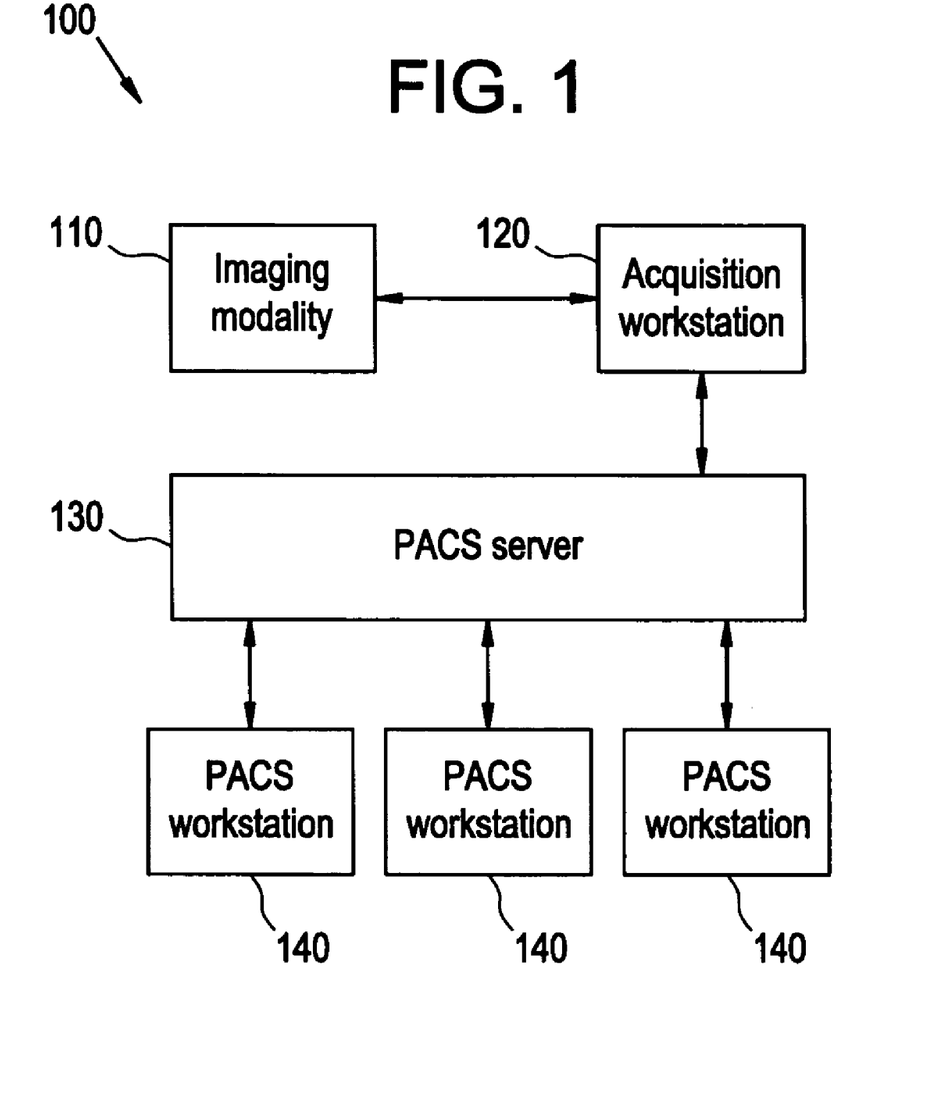
FIG. 1 illustrates an exemplary picture archiving and communication system used in accordance with an embodiment of the present invention.

FIG. 1 illustrates an exemplary Picture Archiving and Communication System (PACS) 100 used in accordance with an embodiment of the present invention. The PACS system 100 includes an imaging modality 110, an acquisition workstation 120, a PACS server 130, and one or more PACS workstations 140. The system 100 may include any number of imaging modalities 110, acquisition workstations 120, PACS server 130 and PACS workstations 140 and is not in any way limited to the embodiment of system 100 illustrated in FIG. 1. The components of the system 100 may communicate via wired and/or wireless communication, for example, and may be separate systems and/or integrated to varying degrees, for example.

In operation, the imaging modality 110 obtains one or more images of a patient anatomy. The imaging modality 110 may include any device capable of capturing an image of a patient anatomy such as a medical diagnostic imaging device. For example, the imaging modality 110 may include an X-ray imager, ultrasound scanner, magnetic resonance imager, or the like. Image data representative of the image(s) is communicated between the imaging modality 110 and the acquisition workstation 120. The image data may be communicated electronically over a wired or wireless connection, for example.

In an embodiment, the acquisition workstation 120 may apply one or more preprocessing functions, for example, to the image data in order to prepare the image for viewing on a PACS workstation 140. For example, the acquisition workstation 120 may convert raw image data into a DICOM standard format or attach a DICOM header. Preprocessing functions may be characterized as modality-specific enhancements, for example (e.g., contrast or frequency compensation functions specific to a particular X-ray imaging device), applied at the beginning of an imaging and display workflow. The preprocessing functions differ from processing functions applied to image data in that the processing functions are not modality specific and are instead applied at the end of the imaging and display workflow (for example, at a display workstation 140).

The image data may then be communicated between the acquisition workstation 120 and the PACS server 130. The image data may be communicated electronically over a wired or wireless connection, for example.

The PACS server 130 may include computer-readable storage media suitable for storing the image data for later retrieval and viewing at a PACS workstation 140. The PACS server 130 may also include one or more software applications for additional processing and/or preprocessing of the image data by one or more PACS workstations 140.

One or more PACS workstations 140 are capable of or configured to communicate with the server 130. The PACS workstations 140 may include a general purpose processing circuit, a PACS server 130 interface, a software memory, and/or an image display monitor, for example. The PACS server 130 interface may be implemented as a network card connecting to a TCP/IP based network, but may also be implemented as a parallel port interface, for example.

The PACS workstations 140 may retrieve or receive image data from the server 130 for display to one or more users. For example, a PACS workstation 140 may retrieve or receive image data representative of a computed radiography ("CR") image of a patient's chest. A radiologist or user may then examine the image for any objects of interest, such as tumors, lesions, etc., for example.

The PACS workstations 140 may also be capable of or configured to apply processing functions to image data. For example, a user may desire to apply processing functions to enhance features within an image representative of the image data. Processing functions may therefore adjust an image of a patient anatomy in order to ease a user's diagnosis of the image. Such processing functions may include any software-based application that may alter a visual appearance or representation of image data. For example, a processing function can include any one or more of flipping an image, zooming in an image, panning across an image, altering a window and/or level in a grayscale representation of the image data, and altering a contrast and/or brightness an image.

In an embodiment, the PACS system 100 may provide one or more perspectives for viewing images and/or accessing applications at a PACS workstation 140. Perspectives may be provided locally at the PACS workstation 140 and/or remotely from the PACS server 130. In an embodiment, the PACS system 100 includes a perspectives manager capable of being used for reviewing images via a plurality of perspectives. The PACS server 130 and/or a PACS workstation 140 may include the perspectives manager, or the perspectives manager may be implemented in a separate system. In an embodiment, each PACS workstation 140 may include a perspectives manager.

A user may wish to apply additional processing steps to one or more images to further enhance features in the image. For example, a user may desire to apply additional processing functions or steps to an image in order to alter the presentation of an image in conformance with the user's confidence level for making an accurate diagnosis. In other words, different users may desire to apply different or additional processing steps than are included in a default image processing workflow.

The additional image processing step(s) may include any image processing step useful to prepare an image for a diagnostic examination. For example, as described above, an image processing step (as a default image processing step or an additional image processing step) can include flipping an image, zooming in an image, panning across an image, and altering one or more of a window, a level, a brightness and a contrast setting of an image.

PACS workstations 140 may retrieve or receive image data from server 130 for display to one or more users. For example, a PACS workstation 140 may retrieve or receive image data representative of a computed radiography image of a patient's chest. A radiologist may then examine the image as displayed on a display device for any objects of interest such as, for example, tumors, lesions, etc.

PACS workstations 140 are also capable of or configured to retrieve and/or receive one or more hanging protocols from server 130. For example, a default hanging protocol may be communicated to PACS workstation 140 from server 130. A hanging protocol may be communicated between server 130 and a PACS workstation 140 over a wired or wireless connection, for example.

In general, PACS workstations 140 may present images representative of image data retrieved and/or received from server 130. PACS workstations 140 may present the images according to a hanging protocol. As described above, a hanging protocol is a set of display rules for presenting, formatting and otherwise organizing images on a display device of a PACS workstation 140. A display rule is a convention for presenting one or more images in a particular temporal and/or spatial layout or sequence. For example, a hanging protocol may include a set of computer-readable instructions (or display rules, for example) that direct a computer to display a plurality of images in certain locations on a display device and/or display the plurality of images in a certain sequence or order. In another example, a hanging protocol may include a set of computer-readable instructions that direct a computer to place a plurality of images in multiple screens and/or viewports on a display device. In general, a hanging protocol may be employed to present a plurality of images for a diagnostic examination of a patient anatomy featured in the images.

A hanging protocol may direct, for example, a PACS workstation 140 to display an anterior-posterior ("AP") image adjacent to a lateral image of the same anatomy. In another example, a hanging protocol may direct PACS workstation 140 to display the AP image before displaying the lateral image. In general, a hanging protocol dictates the spatial and/or temporal presentation of a plurality of images at PACS workstation 140.

A hanging protocol differs from a default display protocol ("DDP"). In general, a DDP is a default workflow that applies a series of image processing functions to image data. The image processing functions are applied to the image data in order to present an image (based on the image data) to a user. The image processing functions alter the appearance of image data. For example, an image processing function may alter the contrast level of an image.

DDPs typically include processing steps or functions that are applied before any diagnostic examination of the images.

For example, processing functions may be applied to image data in order to enhance features within an image (based on the image data). Such processing functions can include any software-based application that may alter a visual appearance or representation of image data. For example, a processing function can include any one or more of flipping an image, zooming in an image, panning across an image, altering a window and/or level setting in a representation of the image data, and altering a contrast and/or brightness setting in a representation of the image data.

DDPs are usually based on a type of imaging modality used to obtain the image data. For example, image data obtained with a C-arm imaging device in general or a particular C-arm imaging device may have a same or similar DDP applied to the image data. In general, a DDP attempts to present image data in a manner most useful to many users.

Conversely, applying a hanging protocol to image data does not alter the appearance of an image (based on the image data), but instead dictates how the image(s) is(are) presented, as described above.

Server 130 may store a plurality of hanging protocols and/or DDPs. The hanging protocols and/or DDPs that are stored at server 130 and have not yet been modified or customized are default hanging protocols/DDPs. A default hanging protocol and/or DDP may be selected from a plurality of default hanging protocols and/or DDPs based on any number of relevant factors such as, for example, a manual selection, a user identity, and/or pre-processing of the image data.

Specifically, a default hanging protocol and/or DDP may be selected based on a manual selection simply by communicating the default protocol once a user has selected that particular protocol. The user may make the selection, for example, at a PACS workstation 140.

In another example, a default protocol may be selected based on a user identity. For example, a user may have a preferred DDP. The DDP may have been customized to meet the user's preferences for a particular temporal and/or spatial layout of images. Once a user gains access to a PACS workstation 140 (for example, by entering a correct login and password combination or some other type of user identification procedure), the preferred DDP may be communicated to the PACS workstation 140, for example.

In another example, a default protocol may be selected based on pre-processing of image data. Pre-processing of image data may include any image processing known to those of ordinary skill in the art that prepares an image for review by a user. Pre-processing may also include, for example, a computer-aided diagnosis ("CAD") of image data. CAD of image data may include a computer (or similar operating unit) automatically analyzing image data for objects of interest. For example, a CAD may include a software application that analyzes image data for nodules in images of lungs, lesions, tumors, etc. However, a CAD application can include any automatic analysis of image data known to those of ordinary skill in the art.

For example, a default hanging protocol that corresponds to CAD findings of lung tumors may provide for the presentation of the posterior-anterior ("PA") and lateral lung images adjacent to each other followed by the presentation of the computer tomography ("CT") lung images, followed by the magnetic resonance ("MR") lung images, for example. In general, a default hanging protocol that corresponds to CAD findings is designed to present images in a spatial and/or temporal layout that is useful to a radiologist. For example, a radiologist may be greatly assisted in his or her review of the CAD findings by viewing the PA and lateral lung images adjacent to each other, followed by previously acquired multi-slice CT and MR images of the lungs.

Therefore, based on CAD findings, a default protocol may be selected from a plurality of default protocols and applied at a workstation 140 in order to present images to a user.

Currently, a user, such as a radiologist or other healthcare practitioner, manually identifies an image matching a currently viewed image in one or more previous exams. That is, for each critical image in a current exam, the radiologist has to manually identify the matching image in each previous exam.

Certain embodiments automate matching of images to previous exam images using registration techniques that allow a mapping between two exams based on anatomy, for example. A registration algorithm may include several parameters including a metric value, for example. The metric value is a measure of similarity between two images. A correlation between two image slices may be directly related to the metric value. Current and previous exam image sets may include one or more images obtained from CT, MR, digital radiography ("DR"), x-ray, ultrasound, nuclear, single phone emission computed tomography ("SPECT"), positron emission tomography ("PET"), and/or other imaging modalities, for example.

Similarity between images may be computed using a variety of metrics. For example, a mean square image to image metric may be used to compute image similarity. The mean square image to image metric quantitatively measures how well a transformed moving image fits a fixed image by comparing a gray-scale intensity of the images. A lower metric value indicates higher correlation between the image slices.

For example, using a mean square difference metric, an image A is compared to images B and C in a previous image set. Each pixel in image A is compared to a corresponding pixel in each of image B and image C. Differences between pixel values are summed for each image and squared. A match metric value for images A and B is then computed by dividing the sum of difference values by the total number of pixels. A match metric value for images A and C is also computed accordingly. A lower metric value indicates fewer differences in pixel values between the images and, therefore, a higher correlation between the images.

Alternatively or in addition, a mutual information metric may be used to compute similarity between images. The mutual information metric measures how much information one random variable (e.g., image intensity in one image) tells about another random variable (e.g., image intensity in the other image).

For example, mutual information may be calculated from a histogram of image intensities for a pair of images A and B. The mutual information metric measures the information shared by image intensity values for pixels in image A and image intensity values for corresponding pixels in image B. A histogram of images intensities for images A and B may show the similarities and differences between image intensities for images A and B. If images A and B are independent, then the mutual information metric value is zero. If images A and B are identical, then image intensities in image A are no different from image intensities in image B, and no new information is added. Mutual information measurements may be used to identify whether image B is the most similar previous image corresponding to image A, for example.

Alternatively or in addition, other metrics, such as normalized correlation, mean reciprocal square difference, cross correlation, minimization of variance, principal axes, manual registration, and/or other registration technique, may be used to identify similar images. In certain embodiments, images of different modalities may be registered using a plurality of metrics.

Exam images may be registered in a variety of ways in order to apply one or more metrics discussed above. Registration techniques may include two-dimensional (2D) axial slice to slice registration and reformat, maximum intensity projection (MIP) and/or scout registration, for example. For a given current and previous exam pair in 2D axial slice to slice registration, each image in the current exam is registered with each image in the previous exam. For example, image slices from the current exam and a previous exam are transformed to a reference coordinate system. Pixel values between the image slices may be compared according to a variety of metrics, including the metrics described above. Corresponding pairs may be identified based on the metric value. For example, an image pair with the lowest metric value is a matching pair. Each image in the current exam may be registered with an image from a previous exam accordingly.

Using reformat/MIP/scout registration, coronal or sagittal reformats, MIPs and/or scout images are generated for the current and previous exams using 2D axial images. Then, using an appropriate translation-rotation transform, the reformat/MIP/scout image(s) for the current exam are registered to the reformat/MIP/scout image(s) for the previous exam. The X and Y coordinate translation values after reformat/MIP/scout registration define a relationship between physical coordinates of the 2D axial images.

For example, an axial image may be reformatted with respect to a certain plane, such as a sagittal or coronal plane. Additionally, an axial image may be analyzed for brightest texture elements (texels) at each pixel location in the image. Furthermore, one or more overview or scout image(s) may be used for comparison with axial image slices. A combination of translation and/or rotation may be used to map pixels in the images to a reference coordinate system. Then images from the current and previous exams may be registered and compared.

Registration and image matching may be computed prior to display of the images on a PACS workstation. When a radiologist or other user opens an exam, hanging protocols may automatically open related previous exams. Using a matching table generated during registration, the radiologist is able to click a button or otherwise select and automatically link images from current and previous exams based on anatomy. Thus, correlation between images from a new exam and images from a previous exam may be performed automatically without manual intervention.

Radiologists and/or other users may link a current exam with multiple previous exams and cine or scroll through exam images with respect to anatomy rather than image number. Images may be synchronized based on a table or other reference listing generated from registering the current exam with the previous exams. A PACS workstation, PACS server, and/or other processing system may be used to automatically determine correlation of images from a patient's previous exam to a new unread exam. In certain embodiments, a user may review linked exam images based on vocal or subvocal command, eye tracking, selection by mousing device, and/or other technique, for example.

In an embodiment, clinical information may also be displayed based on anatomy. For example, a patient may have pathology, lab results, microbiology, historical data, etc. as well as images. When a radiology or other healthcare practitioner is examining images, he or she may wish to also consider clinical information, such as test results, etc. Additionally, results may only be relevant to certain parts of anatomy.

If a PACS determines which images and/or anatomy a practitioner is reviewing, the PACS may automatically display relevant results. A PACS or other system may map results and/or other data with relevant anatomy. The PACS registers viewed image(s) to reference image(s). Based on registration, the PACS may determine anatomy and retrieve relevant data mapped to the anatomy.

Figure 2:
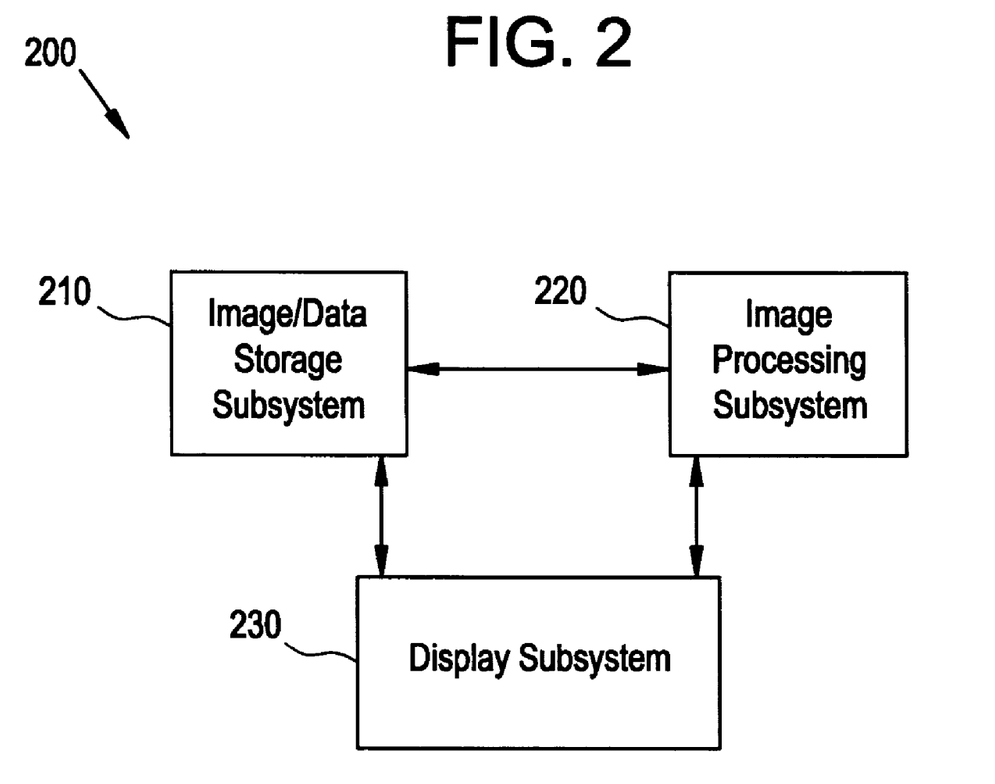
FIG. 2 illustrates an image registration system for registering and comparing exam images to identify corresponding images in accordance with an embodiment of the present invention.

Image registration and correlation may be facilitating using a PACS, such as PACS 100, and/or other processing system. FIG. 2 illustrates an image registration system 200 for registering and comparing exam images to identify corresponding images in accordance with an embodiment of the present invention. The image registration system 200 may be implemented on a PACS workstation, PACS server, image viewer, and/or other processor, for example. Image registration, processing, display, and/or other functionality of the system 200 may be implemented in hardware, firmware, and/or as a set of instructions in software, for example. The system 200 includes an image/data storage subsystem 210, and image processing subsystem 220, and a display subsystem 230. The components of the system 200 may be implemented separately and/or integrated in various forms.

The image/data storage subsystem 210 stores image exams and/or related data, for example. In an embodiment, the image/data storage subsystem 210 may include a matching table, database, or other memory structure indicating a mapping between an image and an historical image for each image in a particular exam. In an embodiment, each exam has an associated matching table or similar structure. In another embodiment, a master matching table includes entries for a plurality of exams.

The image processing subsystem 220 analyzes an image in a current exam and registers that image with all images in a historical exam. A metric value is generated from each registration that indicates a similarity between the two images. In certain embodiments, a lower metric value indicates a higher correlation. In certain embodiments a higher metric value may indicate a higher correlation. A historical image matching the current image is identified based on the metric value. Image analysis is repeated for each image in the current exam until a one to one mapping is determined between current exam images and historical images. However, in certain embodiments, images may exist in the current and/or historical exams with no matching counterpart.

Correlation or matching between images in a current and an historical exam may be mapped and stored in a table, database, data structure, and/or other memory, for example. The mapping, as well the images and associated data, may be stored in the image/data storage subsystem 210, for example. In an embodiment, each exam stored on a system, such as a PACS, has an associated matching table or other mapping reference. A PACS workstation or other viewer retrieves an exam and references the table to retrieve linked historical exam image(s) and/or related data, for example.

In an embodiment, the display subsystem 230 facilitates display of exam image data and facilitates display of linked historical image(s) and/or other data in relation to the exam image data. Current exam image(s), related historical image(s), and/or relevant clinical data may be provided to a user via the display subsystem 230, such as via a monitor and/or other screen.

Figure 3:
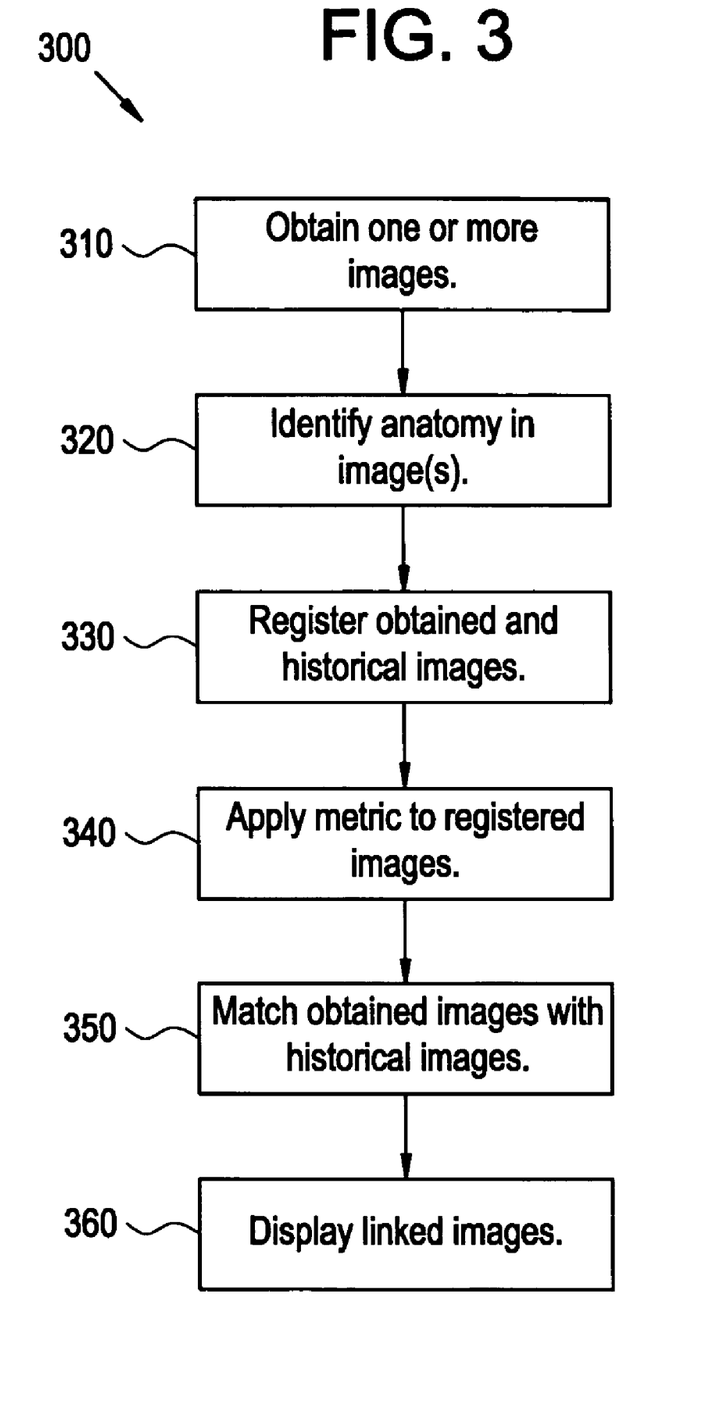
FIG. 3 illustrates a flow diagram for a method for image registration and correlation based on image anatomy used in accordance with an embodiment of the present invention.

FIG. 3 illustrates a flow diagram for a method 300 for image registration and correlation based on image anatomy used in accordance with an embodiment of the present invention. First, at step 310, one or more images are obtained. For example, an exam including a plurality of image slices of a patient may be obtained from an imaging modality. Then, at step 320, major organs and/or other anatomical parts of interest may be identified for each image in an exam. For example, heart, lungs, liver, kidneys, etc. may be identified in a series of images obtained for a patient.

Next, at step 330, the one or more obtained images are registered with one or more historical exam images. For example, a currently obtained image set for a patient may be registered with a previous image set for that patient and/or with a reference image set. A plurality of registration techniques, such as techniques from the National Library of Medicine ITK registration toolkit, 2D axial slice-to-slice registration, reformat/MIP/scout registration, etc., may be used to register the obtained and historical images.

At step 340, one or more metrics are applied to the registered images. For example, one or more metrics, such as a mean square image to image metric, a mutual information metric, a cross correlation metric, etc., are applied to image data in a newly obtained image and one or more historical images to generate a metric value or result for comparison. Then, at step 350, newly obtained images are matched with historical images based on metric values. For example, a new-historical image pair having a lowest metric value is identified as a corresponding pair of similar images. Corresponding pairs may be identified for the entire exam. Correspondence information may be stored in a table, database, data structure, memory, etc., and/or as image meta-data, for example. At step 360, obtained images and corresponding linked historical images are displayed for a user. Thus, a user may review newly obtained exam images along with corresponding historical images.

Certain embodiments may be provided as a set of instructions residing on a computer-readable medium, such as a memory or hard disk, for execution on a computer or other processing device, such as a PACS workstation or image viewer.

Thus, certain embodiments provide automatic analysis and linking of images from current and previous exams based on anatomy. Correlations between current and historical images may be performed automatically without manual selection or intervention. Certain embodiments allow a radiologist to link a current exam with one or more previous exams and move through the exam images with respect to anatomy instead of or in addition to image number. Certain embodiments facilitate exam registration and correlation via a PACS workstation and/or image viewer, for example.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An image registration system for correlating a current image with a previous image, said system comprising:
an image processing subsystem configured to identify anatomical parts of interest on at least one current image of a patient's anatomy, the at least one current image obtained by an image modality during a medical exam of the patient, and register the at least one current image of the patient from the current medical exam with at least one image from a previous medical exam of the patient and compare the at least one current image and at least one previous image using a metric that measures the similarity of the at least one current image and the at least one previous image based on the anatomical parts of interest in the at least one current image and the at least one previous image, wherein said image processing subsystem identifies a corresponding previous image for a current image based on said metric, wherein said metric is a mean square image-to-image metric that compares gray-scale intensity of the at least one current image with the at least one previous image, wherein a lower metric value indicates a higher correlation between the images; and
a matching table identifying said current image and said corresponding previous image, wherein said matching table is used to automatically retrieve said corresponding previous image when said current image is displayed,
wherein said matching table is configured for use with a user interface for user selection to automatically link said current image and said corresponding previous image for display.

2. The system of claim 1, wherein said metric generates a metric value representing a degree of similarity between said at least one current image and said at least one previous image, and wherein said image processing subsystem identifies a corresponding previous image for a current image based on said metric value.

3. The system of claim 1, wherein said image processing subsystem registers said at least one current image and said at least one previous image according to a coordinate system.

4. The system of claim 1, further comprising a display subsystem configured to display said current image in conjunction with said corresponding previous image.

5. The system of claim 4, wherein said display subsystem is configured to display clinical data in conjunction with said current image and said corresponding previous image.

6. The system of claim 1, further comprising an image/data storage subsystem configured to store at least one of said at least one current image, said at least one previous image, and clinical data.

7. The system of claim 1, wherein said image processing subsystem automatically identifies a corresponding previous image for a current image upon receipt of said current image.

8. A computer-implemented method for automatically correlating anatomy in an acquired image with an historical image, said method comprising:
acquiring at least one image of a patient's anatomy during a medical exam;
automatically identifying anatomical parts of interest on the at least one acquired image by the computer;
registering, using the computer, the at least one acquired image of the patient with at least one historical image from a previous medical exam of the patient that is similar to the at least one acquired image according to a coordinate system;
applying a metric to said at least one acquired image and said at least one historical image, wherein said metric is based on a mutual information metric that measures how much information one random variable in one of the at least one acquired image indicates about that variable in at least one of the at least one historical image, and wherein the metric generates a metric value representing a degree of similarity between the at least one acquired image and the at least one historical image based on similarity of anatomical parts of interest in the at least one acquired image and the at least one historical image;
identifying, without manual intervention, a correlation between one of said at least one acquired image and one of said at least one historical image based on said metric and storing said correlation in a matching table identifying said acquired image and said corresponding at least one historical image, wherein said matching table is used to automatically retrieve said corresponding historical image when said acquired image is displayed, wherein said matching table is configured for use with a user interface for user selection to automatically link said acquired image and said corresponding historical image for display;

automatically linking said acquired image and one of said at least one historical image based on said correlation; and displaying said acquired image and one of said at least one historical image based on said correlation.

9. The computer-implemented method of claim 8, further comprising storing, via said computer, said correlation between said acquired image and one of said at least one historical image for automatic linking of said acquired image and one of said at least one historical image upon display.

10. The computer-implemented method of claim 8, wherein said metric is based on a mean square image-to-image metric that compares gray-scale intensity of the at least one current image with the at least one previous image, wherein a lower metric value indicates a higher correlation between the images.

11. A computer-readable storage medium including a set of instructions for execution on a processor, the set of instructions comprising:

an image registration routine configured to register an acquired image taken of a patient's anatomy during a medical exam with respect to at least one historical image of the patient's anatomy from a previous exam; and an image mapping routine configured to map said acquired image with one of said at least one historical image based on anatomy, wherein said image mapping routine identifies one of said at least one historical image similar to said acquired image based on a metric that generates a metric value representing a degree of similarity between said acquired image and said at least one historical image based on similarity of anatomical parts of interest, wherein said metric is a mutual information metric that measures how much information one random variable in said acquired image indicates about that variable in said one of said at least one historical image;

a mapping data structure, wherein said mapping data structure stores a mapping between said acquired image and said one of said at least one historical image; and a display routine to display said acquired image and said one of said at least one historical image.

12. The computer-readable storage medium of claim 11, wherein said display routine automatically displays said acquired image and said one of said at least one historical image based on a mapping of said acquired image with said one of said at least one historical image.

13. The computer-readable storage medium of claim 11, wherein said image mapping routine further identifies and displays clinical information relevant to at least one of said acquired image and said one of said at least one historical image.

14. The computer-readable storage medium of claim 11, wherein said image mapping routine automatically links said acquired image and said one of said at least one historical image for display.

15. The system of claim 1, wherein said metric further comprises a mutual information metric that measures how much information one random variable in one of the at least one current or previous images indicates about that variable in the other of the at least one current or previous images.

\* \* \* \* \*